US012749075B2

(12) United States Patent
Poteet, III et al.

(10) Patent No.: US 12,749,075 B2
(45) **Date of Patent: *Sep. 29, 2026**

(54) PROVIDING A FINANCIAL/CLINICAL DATA INTERCHANGE

(71) Applicant: CERNER INNOVATION, INC., Kansas City, MO (US)

(72) Inventors: James L. Poteet, III, Overland Park, KS (US); Vidya Nv, Kerala (IN); Venkata Nageswara Rao Desaraju, Bangalore (IN); Roma Kumari, Jharkhand (IN); Pogaku Shahazad, Bangalore (IN); Mandar Vijay Kulkarni, Maharashtra (IN); Sparsha Shetty, Bangalore (IN)

(73) Assignee: CERNER INNOVATION, INC., Kansas City, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 19/369,652

(22) Filed: Oct. 27, 2025

(65) Prior Publication Data

US 2026/0050918 A1 Feb. 19, 2026

Related U.S. Application Data

(63) Continuation of application No. 18/067,965, filed on Dec. 19, 2022, now Pat. No. 12,488,337, and a (Continued)

(30) Foreign Application Priority Data

Apr. 24, 2019 (IN) ............................ 201911016297

(51) Int. Cl.

*G06Q 20/38* (2012.01)
*G06Q 20/40* (2012.01)
*G16H 10/60* (2018.01)

(52) U.S. Cl.

CPC ....... *G06Q 20/3829* (2013.01); *G06Q 20/401* (2013.01); *G16H 10/60* (2018.01); *G06Q 2220/00* (2013.01)

(58) Field of Classification Search

None

See application file for complete search history.

(56) References Cited

U.S. PATENT DOCUMENTS

2015/0332283 A1* 11/2015 Witchey ................ G16H 10/60 705/3
2017/0161439 A1* 6/2017 Raduchel ............... H04W 4/02

(Continued)

*Primary Examiner* — Jamie R Kucab

(74) *Attorney, Agent, or Firm* — Kraguljac Law Group LLC

(57) ABSTRACT

Systems and methods for providing a financial/clinical data interchange are provided. The financial/clinical data interchange provides a distributed implementation to a secure hash key (i.e., a token) and value pair data derived from a medical claim (e.g., patient identification, submitter identification, payer identification, encounter identification, and the like) and enriched with submitter-based domain data. The token may be used as a data attribute in an API that unlocks a pointer to the value (e.g., a fast healthcare interoperability resources (FHIR) uniform resource identifier (URI) to the patient encounter associated with the claim) to leverage a FHIR query for all documented medical records associated with the claim the payer is authorized by the submitter to view.

17 Claims, 6 Drawing Sheets

Related U.S. Application Data continuation of application No. 16/457,320, filed on Jun. 28, 2019, now Pat. No. 11,568,397.

(56) References Cited

U.S. PATENT DOCUMENTS

| | | | | |
|---|---|---|---|---|
| 2019/0340013 | A1* | 11/2019 | Cella | G06Q 10/04 |
| 2020/0211409 | A1* | 7/2020 | Latorre | G16H 10/60 |
| 2021/0097602 | A1* | 4/2021 | Eichel | G06Q 20/0855 |

* cited by examiner

PROVIDING A FINANCIAL/CLINICAL DATA INTERCHANGE

CROSS-REFERENCE TO RELATED APPLICATIONS

This application is a continuation of U.S. application Ser. No. 18/067,965 filed Dec. 19, 2022, which is a continuation of U.S. application Ser. No. 16/457,320 filed Jun. 28, 2019 entitled “Providing a Financial/Clinical Data Interchange”, now U.S. Pat. No. 11,568,397, and claims the benefit of Indian Provisional Application No. 201911016297, filed Apr. 24, 2019, and entitled “Providing a Financial/Clinical Data Interchange,” which are all hereby incorporated by reference in their entirety.

BACKGROUND

In healthcare today, claims form a primary part of the financial aspect of any health care system. In these systems, a significant amount of information is often shared between payers and submitters for claim processing. Given that the number of claims sent by submitters is very large, when a payer needs any additional information for a single claim, the payer must contact the respective submitter.

For example, a subset of claims may be received by the payer. To process a claim from the subset of claims, the payer may need some additional clinical information. In such a scenario, the payer requests additional clinical information from the submitter. In present systems, this is often facilitated by a third party. The submitter provides the additional clinical information to the payer. This process often requires multiple requests until the payer receives the necessary information to process the claim. Each of these transactions is supported through the third party and, in addition to being cumbersome and inefficient with respect to time as well as computing and personnel resources, the transactions also add additional costs to claim processing, and the health care system generally.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems and methods of providing a financial/clinical data interchange. More particularly, a financial/clinical data interchange provides a distributed implementation to a secure hash key (i.e., a token) and value pair data derived from a medical claim (e.g., patient identification, submitter identification, payer identification, encounter identification, and the like) and enriched with submitter-based domain data. The token may be used as a data attribute in an API that unlocks a pointer to the value (e.g., a fast healthcare interoperability resources (FHIR) uniform resource identifier (URI) to the patient encounter associated with the claim) to leverage a FHIR query for all documented medical records associated with the claim the payer is authorized by the submitter to view.

DETAILED DESCRIPTION

Figure 1:
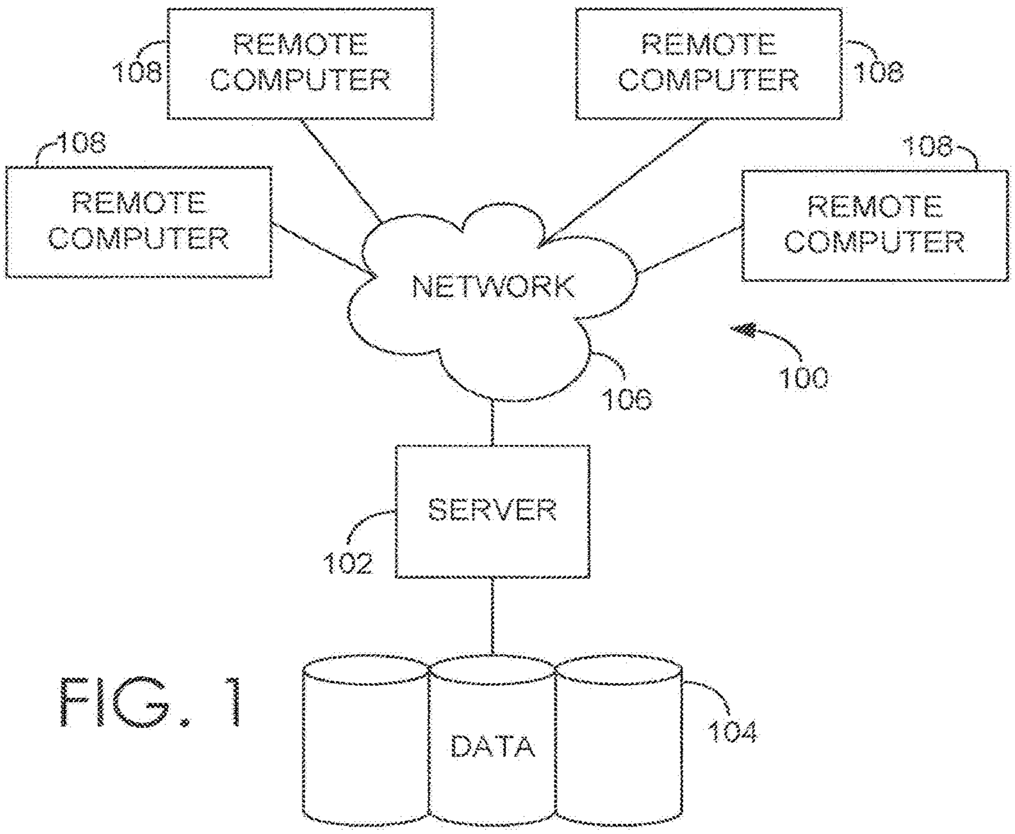
FIG. 1 is a block diagram of an exemplary operating environment suitable to implement embodiments of the present system/method.

The subject matter of the present system/method is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms “step” and/or “block” might be used herein to connote different elements of methods employed, the terms should not be interpreted as implying any particular order among or between various steps herein disclosed unless and except when the order of individual steps is explicitly stated.

Various terms are used throughout this description. Definitions of some terms are included below to provide a clearer understanding of the ideas disclosed herein:

A blockchain is a decentralized network of multiple peers sharing an immutable and incorruptible ledger copy that records every transaction occurring in the channel. Each node in the network carries a copy of the ledger. If one node updates the ledger, all the ledger copies in the network are updated. An append-only nature of the blockchain means that once a transaction has occurred and is added to the ledger, it can never be tampered with or removed.

Each block in the blockchain contains three main components: data, a hash of the previous block, and a hash of the current block. The hash generated for the current block is also added at the beginning of the next block, forming an irreversible chain of blocks that are immune to any tampering. A block is generated and added to blockchain for every transaction that occurs in the blockchain network.

A submitter corresponds to any clinician, health care practice, health care facility, or provider seeking reimbursement for medical care via a claim.

A payer represents an insurance carrier, health plan sponsor, or other third-party payers that finance or reimburse the cost of health services provided to a patient.

A medical claim (e.g., an ANSI ASCX12N 837 claim) is used to submit healthcare payments, billing information, encounter information, or a combination, by a payer or submitter and is transmitted electronically to the payer or submitter.

As noted in the background, in healthcare today, claims form a primary part of the financial aspect of any health care system. In these systems, a significant amount of information is often shared between payers and submitters for claim processing. Given that the number of claims sent by submitters is very large, when a payer needs any additional information for a single claim, the payer must contact the respective submitter.

For example, a subset of claims may be received by the payer. To process a claim from the subset of claims, the payer may need some additional clinical information. In such a scenario, the payer requests additional clinical information from the submitter. For example, clinical data may be needed to give prior authorization for a particular service or treatment. In another example, a payer may request clinical information to ensure billing accuracy. In some instances (e.g., Medicare Advantage), providers may be contractually required to submit clinical information for quality ratings (e.g., healthcare effectiveness data and information set (HEDIS) and star ratings) and risk adjustments. Early intervention and disease management, care coordination, population health and member attribution may be other additional reasons that payers request clinical information.

In present systems, this is often facilitated by a third party, for a fee. The submitter provides the additional clinical information to the payer. This process often requires multiple requests until the payer receives the necessary information to process the claim. Each of these transactions is supported through the third party and, in addition to being cumbersome and inefficient with respect to time as well as computing and personnel resources, the transactions also add additional costs to claim processing, and the health care system generally.

Embodiments of the present disclosure relate to systems and methods for providing a financial/clinical data interchange. The financial/clinical data interchange provides a distributed implementation to a secure hash key (i.e., a token) and value pair data derived from a medical claim (e.g., patient identification, submitter identification, payer identification, encounter identification, and the like) and enriched with submitter-based domain data. The token may be used as a data attribute in an API that unlocks a pointer to the value (e.g., a fast healthcare interoperability resources (FHIR) uniform resource identifier (URI) to the patient encounter associated with the claim) to leverage a FHIR query for all documented medical records associated with the claim the payer is authorized to view. Each participating payer may have their own node in the chain. Payers can leverage their node to query data in the chain which may provide greater efficiencies by offloading those transactions from a central system. In embodiments, the blockchain may be implemented such that any submitter and payer may participate using their own key-value pair to enable a medical records transaction.

In implementation, a token into a medical claim as it is added to the enterprise blockchain network. The token can be extracted from the claim and used as an input for an API that returns a FHIR URI. The FHIR URI is a generated exact query to access the patient's clinical data associated with the specific medical claim. This enables the data to be queried from where it resides in the origin system rather than transported via protocol exchange. In addition to the added efficiencies, this process is also more secure than transporting data via various system intermediaries.

The enterprise blockchain network provides both a seamless and secure process of data sharing. Transaction and processing costs for information exchange between payers and submitters can be avoided using the enterprise blockchain network. Additionally, the need for third party mediators to facilitate these transactions is eliminated. Generally, resource sharing, based on roles, can be facilitated for submitters and payers on the enterprise blockchain network. Business logic further facilitates these transactions. According to an endorsement policy set by the network, peers validate transactions and are identified using cryptography keys.

As a result, significant cost savings, approximated at fifteen to eighty percent of current costs, are realized. Payers do not need to wait for submitters to send additional information and submitters do not need to verify and send additional clinical information for every claim when requested by the payers, enabling provider staff to remain focused on care delivery. Since this is a standards based approach, leveraging existing HIPAA and FHIR standards, there is not vendor lock-in. Moreover, inefficient and friction-based transactions that do not add any value to healthcare are significantly reduced or eliminated. Transparency is enabled for all parties and accuracy, data privacy, and security compliance is increased while the duration of data retrieval is reduced. Participants in the data retrieval value chain are reduced to one provider and one payer, thus eliminating the third party.

Overall efficiencies within the respective health data network are also gained (i.e., web services data retrieval pattern vs. HL7 interchange with enterprise-wide master patient index (EMPI) searches). The enterprise blockchain network also enables any healthcare information technology provider to participate by leverage a key-value pair with participating payers. Patients may also benefit from participating in the interchange by monitoring who has accessed their clinical records as well as the status of their claims.

Accordingly, one embodiment of the present disclosure is directed to a system for providing a financial/clinical data interchange. The system includes a processor; and a computer storage medium storing computer-usable instructions that, when used by the processor, cause the processor to: receive a selection of clinical information types for a claims file; add a hash key generated upon insertion of the data into a blockchain to the claims file; authenticate payers to use a blockchain UI or API; render a payer API that enables a payer of the payers to send GET requests comprising parameters to query content from the blockchain, the parameters comprising a payer ID and the hash key, wherein the hash key is obtained from the claims file.

In another embodiment, the present disclosure directed to a computerized method for providing a financial/clinical data interchange. The method includes receiving a selection of clinical information types for a claims file. The method also includes adding a hash key generated upon insertion of the data into a blockchain to the claims file. The method further includes authenticating payers to use a blockchain UI or API. The method also includes rendering a payer API that enables a payer of the payers to send GET requests comprising parameters to query content from the blockchain, the parameters comprising a payer ID and the hash key, wherein the hash key is obtained from the claims file.

In yet another embodiment, the present disclosure is directed to one or more computer storage media having computer-executable instructions embodied thereon that, when executed by a computer, causes the computer to perform operations to provide a financial/clinical data interchange. The operations include receiving a selection of clinical information types for a claims file. The operations also include adding a hash key generated upon insertion of the data into a blockchain to the claims file. The operations further include authenticating payers to use a blockchain UI or API. The operations also include rendering a payer API that enables a payer of the payers to send GET requests comprising parameters to query content from the blockchain, the parameters comprising a payer ID and the hash key, wherein the hash key is obtained from the claims file.

Having briefly described embodiments of the present system/method, an exemplary operating environment suitable for use in implementing embodiments of the present system/method is described below. FIG. 1 provides an aspect of an example operating environment with which embodiments of the present system/method may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, database cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

In some embodiments, remote computers 108 comprise computing-devices that are part of a cloud-computing platform. For example, the control server 102 might operate in a computer network 106 hosted as part of a cloud service (e.g., AMAZON WEB SERVICES, GOOGLE HOSTING, IBM BLUEMIX). In some embodiments, a remote computer 108 is associated with a health records data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
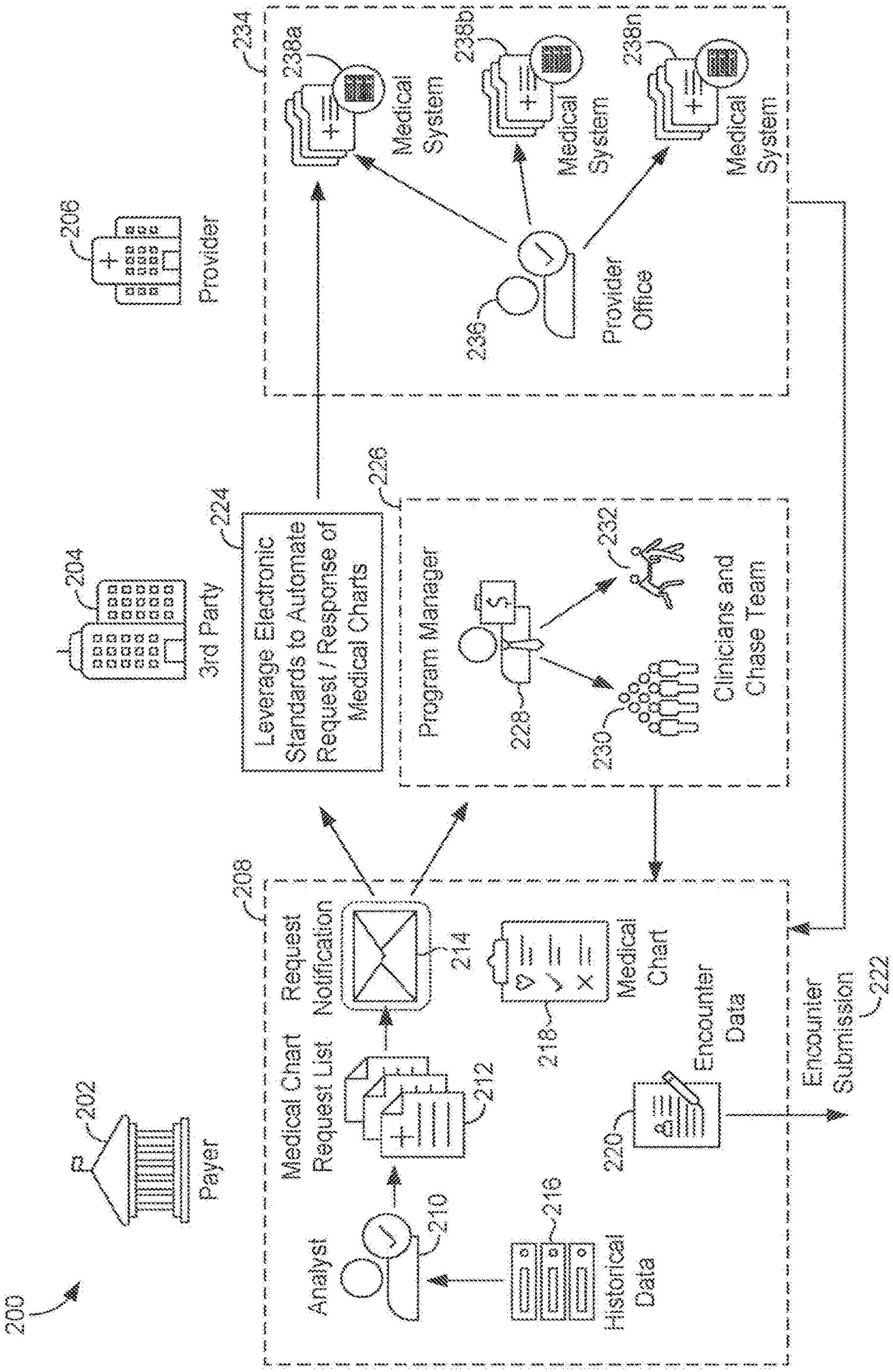
FIG. 2 depicts an exemplary framework of an interchange system suitable to implement embodiments of the present system/method.

Turning now to FIG. 2, an exemplary framework of an interchange system 200 is shown, in accordance with an aspect of the present system/method. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The interchange system 200 may be implemented via any type of computing device, such as computing device 100 described above with reference to FIG. 1, for example.

The interchange system 200 generally operates to provide more efficient sharing of clinical information in claim processing and reduces intermediary costs associated with previous systems. As shown in FIG. 2, the interchange system 200 includes, among other components not shown, a payer system 208, an interchange 224, and a provider system 234. It should be understood that the interchange system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of patient payer or provider systems may be employed within the interchange system 200 within the scope of the present disclosure. Each may comprise a single device or multiple devices cooperating in a distributed environment. For instance, the payer system 208 may be provided via multiple devices arranged in a distributed environment that collectively provide the functionality described herein. In other embodiments, a single device may provide the functionality of multiple components of the payer system 208. Additionally, other components not shown may also be included within the network environment.

Generally, with reference to FIG. 2, the payer system 208 enables the payer 202 to request clinical information from a provider 206. The payer system 208 may enable an analyst 210 to initially access historical data 216. The analyst 210 may determine additional clinical information is needed. Accordingly, the analyst 210 may identify the clinical information is a medical chart request list 212. The medical chart request list 212 is submitted to the provider in a request notification 214. As illustrated, the interchange 224 enables the payer to bypass the third party 204 that previous systems required. Additionally, the third party system 226 that required, for example, a program manager, clinicians 230, and a chase team 232 to track down the clinical information are also obviated by the interchange 224.

In this way, the interchange 224 receives the request notification 214 and communicates it to the provider system 234. The provider system may enable a provider office 236 to document various clinical information into one or more medical systems 238*a*, 238*b*, 238*n*. As described in more detail below, the interchange 224 enables the request notification 214 to directly link to and retrieve the appropriate information from the appropriate medical system. Once the payer 202 has the necessary information from the retrieved medical chart 218, the information can be added to the encounter data 220 and the encounter 222 can be processed for payment.

Figure 3:
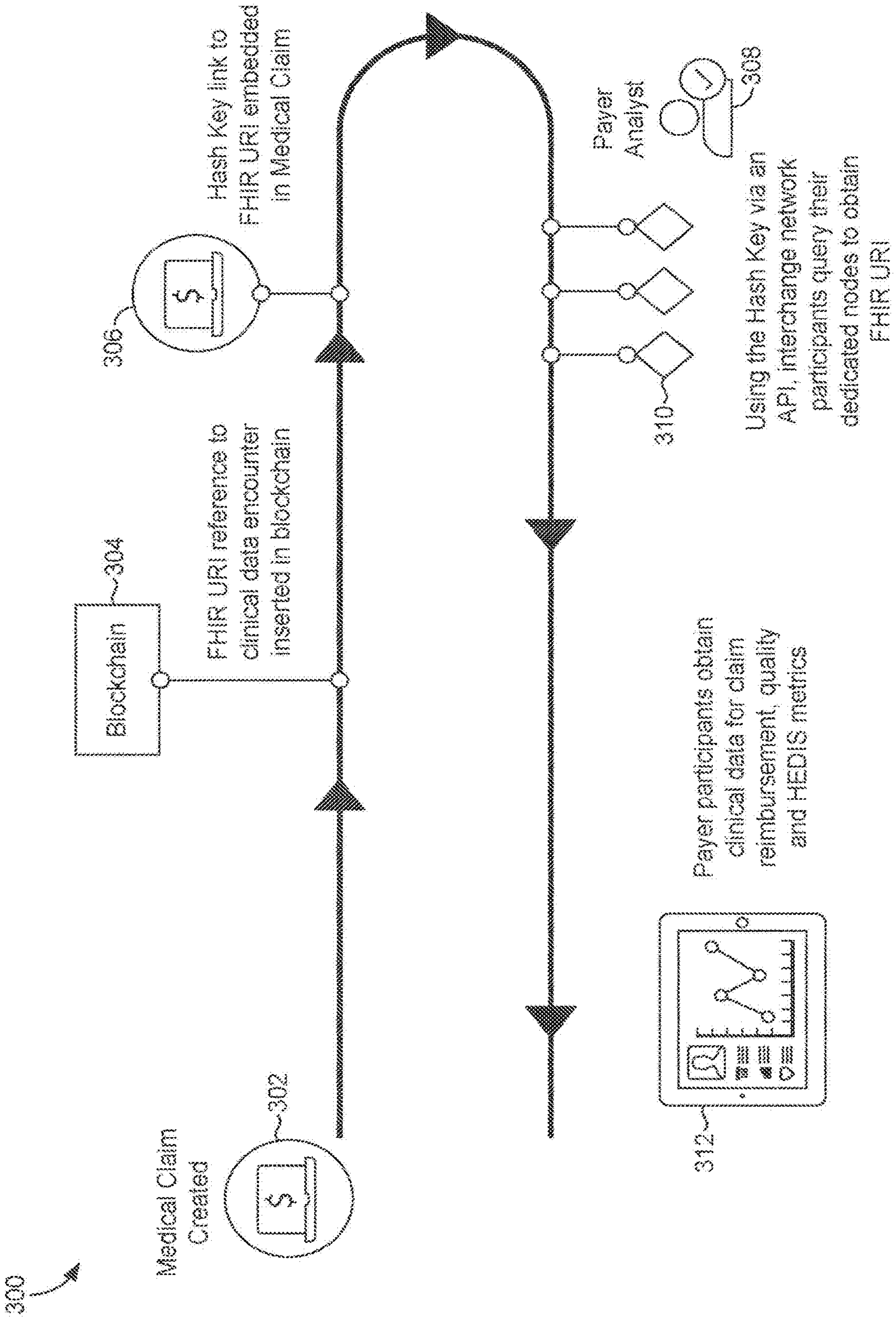
FIG. 3 is a flow diagram of an exemplary method for providing an interchange system, in accordance with an embodiment of the present system/method.

Referring now to FIG. 3, a flow diagram is provided illustrating an exemplary method for providing an interchange system, in accordance with an embodiment of the present system/method. Method 300 may be performed by any computing device (such as computing device described with respect to FIG. 1) with access to an interchange system (such as the one described with respect to FIG. 2) or by one or more components of the interchange system.

Initially, at step 302, a medical claim is created. A FHIR URI reference to the clinical data encounter corresponding to the medical claim is inserted into the interchange, at step 304. At step 306, a hash key link to the FHIR URI is embedded in the medical claim. Upon a payer analyst 308 determining that clinical information is needed to process a claim, at step 310, the hash key in the medical claim is utilized via an API to query the payer's dedicated node to obtain the FHIR URI. At step 312, the payer obtains the clinical data needed for claim reimbursement, preauthorization, quality metrics, and the like.

Figure 4:
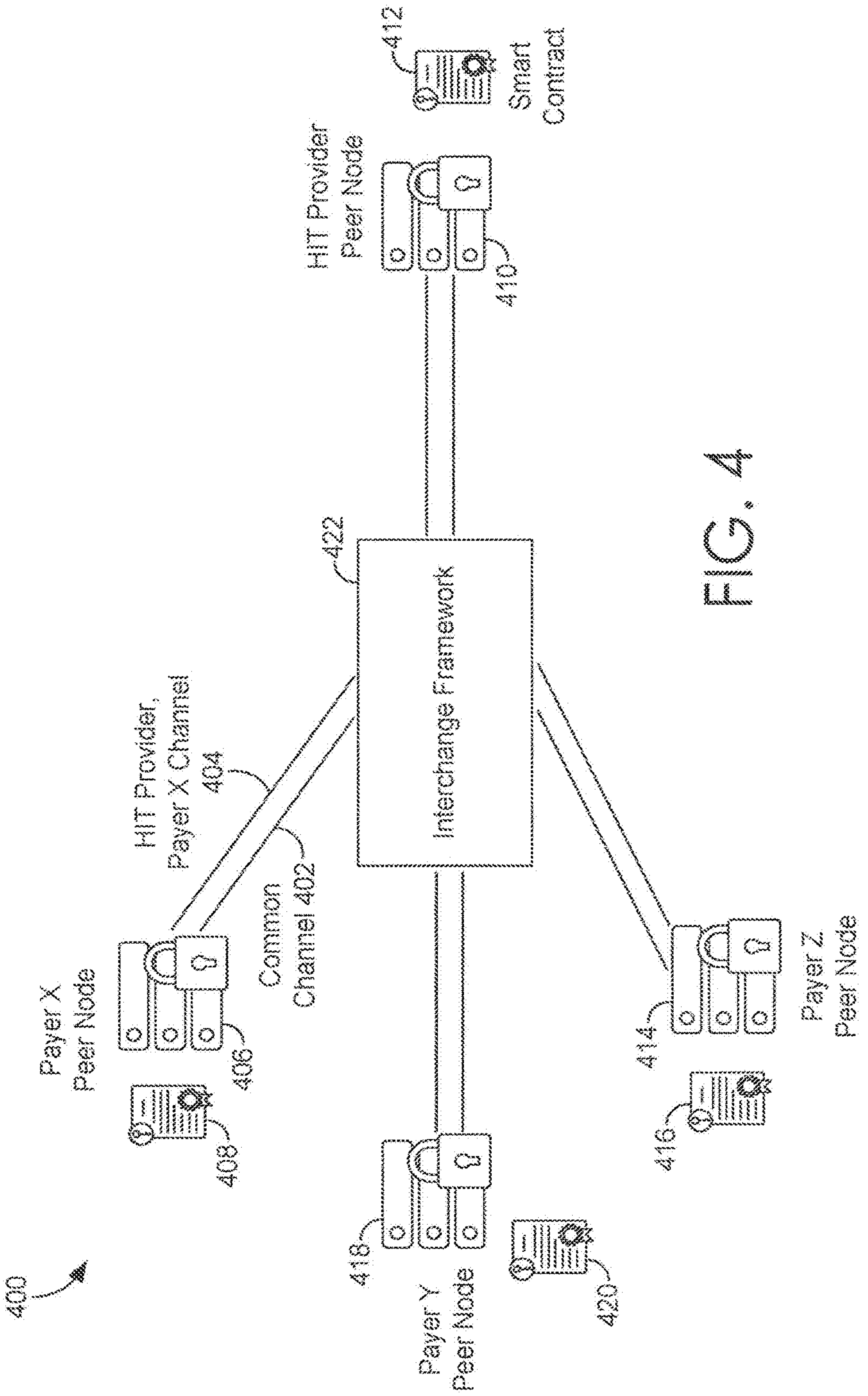
FIG. 4 is an exemplary framework of the nodes participating in the interchange system, in accordance with embodiments of the present system/method.

Turning now to FIG. 4, an exemplary framework of the nodes participating in the interchange system 400 is shown, in accordance with an aspect of the present system/method. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The interchange system 400 may be implemented via any type of computing device, such as computing device 100 described above with reference to FIG. 1, for example.

The interchange system 400 generally operates to provide a data interchange between payer and submitter participants. As shown in FIG. 4, the interchange system 400 includes, among other components not shown, payer X peer node 406, healthcare information technology (HIT) provider peer node 410, payer Z peer node 414, payer Y peer node 418, interchange fabric 422, payer X channel 404, and common channel 402. It should be understood that the interchange system 400 shown in FIG. 4 is an example of one suitable computing system architecture. Each of the components shown in FIG. 4 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of patient accounting components, analytics components, financial hubs, or payer/partner systems may be employed within the interchange system 400 within the scope of the present disclosure. Each may comprise a single device or multiple devices cooperating in a distributed environment. For instance, each of the nodes (e.g., provider peer node 410, payer Z peer node 414, payer Y peer node 418, interchange fabric 422) may be provided via multiple devices arranged in a distributed environment that collectively provide the functionality described herein. Additionally, other components not shown may also be included within the network environment.

Generally, with reference to FIG. 4, interchange fabric 422 enables payers and providers (i.e., submitters) to share data on the interchange system. As shown, each payer has its own node or set of nodes (e.g., payer X peer node 406, payer Z peer node 414, payer Y peer node 418) and its own channel for each provider the payer participates in the exchange with (e.g., payer X channel 404). This enables smart contract code execution (e.g., smart contract 408, 412, 416, 420) to only add blocks to the appropriate node for each provider/payer combination. For example, a smart contract 412 between provider and payer X would only cause blocks to be written to payer x peer node 406. Similarly, smart contract 408 enables payer X to communicate with HIT provider peer node 410, rather than another provider's node. The common channel 402 is utilized to synchronize all nodes in the interchange system 400.

Figure 5:
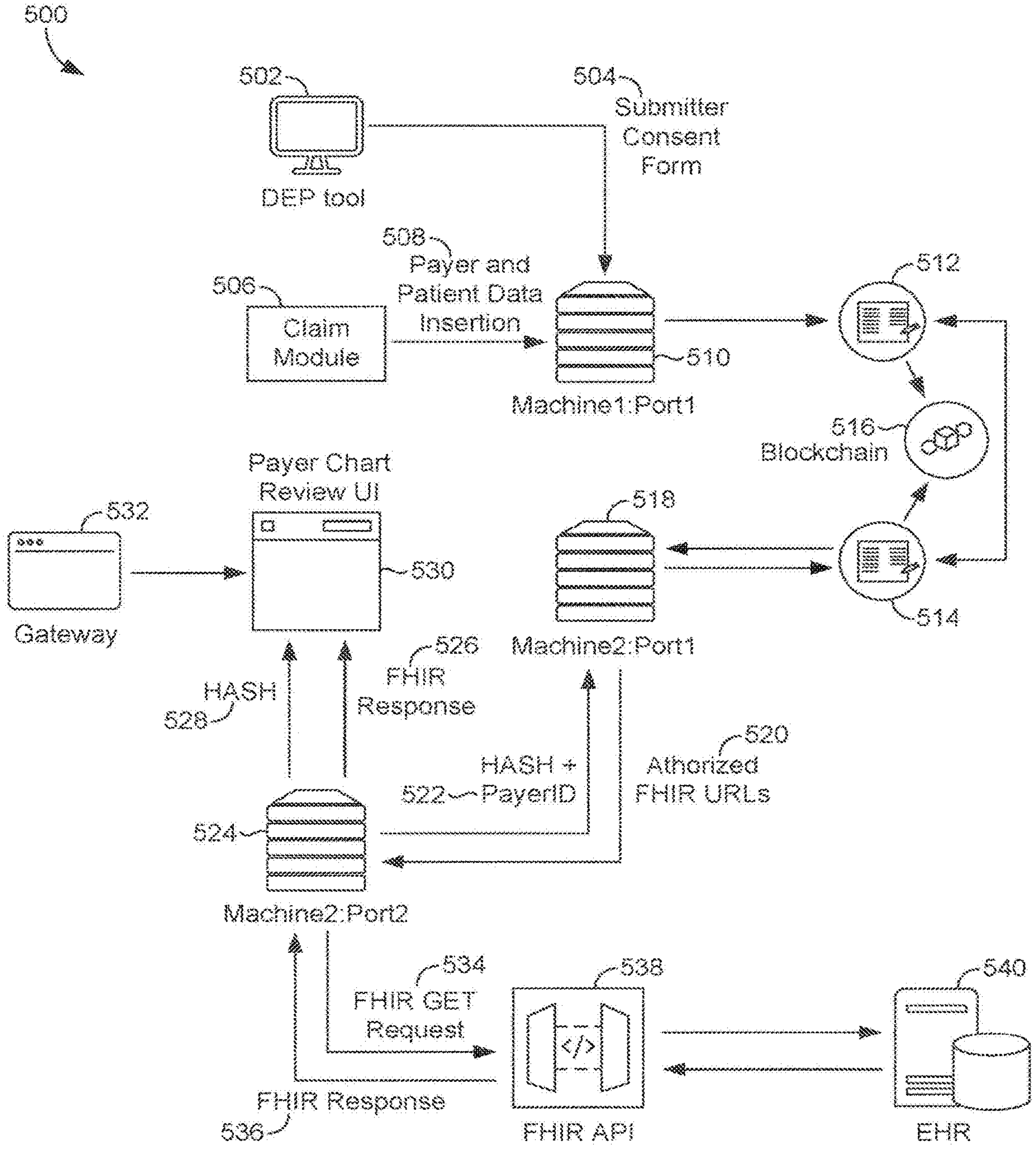
FIG. 5 is a flow diagram of a method for utilizing the interchange system, in accordance with embodiments of the present system/method.

In FIG. 5, a flow diagram is provided illustrating a method 500 for utilizing the interchange system, in accordance with embodiments of the present system/method. Method 500 may be performed by any computing device (such as computing device described with respect to FIG. 1) with access to an interchange system (such as the one described with respect to FIG. 2) or by one or more components of the interchange system.

Initially, at step 502, a data exchange partner (DEP) tool provides a gateway for a submitter to subscribe to the interchange system. A Submitter may select types of clinical information a payer is allowed to see and sign a consent for the payer to view the data, which forms consent data. The submitter consent form 504 and the selected types of allowed clinical information (e.g., consent data) are stored by invoking a smart contract 512 in the blockchain 516. This information acts as the reference point for a payer invoking a smart contract 514 to retrieve clinical information.

For every claim file generated, at step 506, the claim module checks to determine the payer and submitter are subscribed to the blockchain. If the check confirms the parties are subscribed, then a clinical information pointer is inserted in the blockchain by a blockchain transaction, via machine1:port 1 510, at step 508, using an insert function with payer and submitter details. A hash value of these details is returned and serves as a unique identifier of the inserted pointer. The claim module then appends the hash value in the claim file that is communicated to the payer. The payer may use this hash to further refer to the additional clinical information using a payer API or payer chart review UI 530.

The blockchain network contains the participating peers in the channel. Cryptographic certificates are generated for all peers and used for digital signature and verification of all transactions in the blockchain network. Smart contracts serve as the primary business logic of the blockchain network. The smart contracts handle the validations and the insertions and queries of the data stored on the blockchain network. Storing huge amounts of medical data on the blockchain network makes the retrieval of data costly and involves the risk of storing protected health information. For this reason, only reference pointers to the additional clinical information are actually stored in the blockchain. These reference pointers are constructed using FHIR API's which retrieves the additional clinical information.

An endorsement policy of the blockchain network comprises peers that need to sign the transactions to make them valid. For every transaction on the blockchain network, a request is sent to all the endorsing peers to sign the transaction. A transaction must be endorsed to be considered valid and only valid transactions are added to the blockchain network. The endorsement policy may be defined while instantiating the smart contracts in the blockchain network. Membership service providers may also be used to generate and verify the cryptographic signatures of the peers on a blockchain transaction.

Gateway 532 provides both a gateway and an authentication mechanism for the payer chart review UI 530. A subscribed payer can utilize the gateway to the blockchain as clinical data interchange via FHIR which redirects to the payer chart review UI 530. The payer chart review UI receives the hash 528 as an input via machine 2:port 2 524 and performs three levels of validations involving the hash, a PayerID, and the PayerID and the hash 522 using the smart contract 514 via machine2:port1 518. If the associated payer does not have access to the hash, then the clinical information is not provided. If the associated payer does have access to the hash the FHIR GET request 534 requests the data via the FHIR API 538 from the EHR 540, the types of clinical information the payer can view that has been allowed by the submitter is provided via the FHIR response 536 to machine 2:port 2 524. The payer may view the clinical information via the payer chart review UI 530 after the FHIR response 526 is communicated by machine 2:port 2 524 and the claim can be processed. In embodiments, a REST API responds with JSON objects containing all valid requests of authorized data (e.g., procedure data, diagnostic reports, observations, document references, medication orders, and the like).

In practice, the blockchain network is initially started and business logic (i.e., smart contracts) is instantiated on the network. The blockchain network hosted on the participating machines each have their own node servers hosting the API calls to send POST and GET requests that insert and query the data from the blockchain network. When data is inserted, a block is generated on all machines and the blockchain network ensures the ledgers are synchronized.

Figure 6:
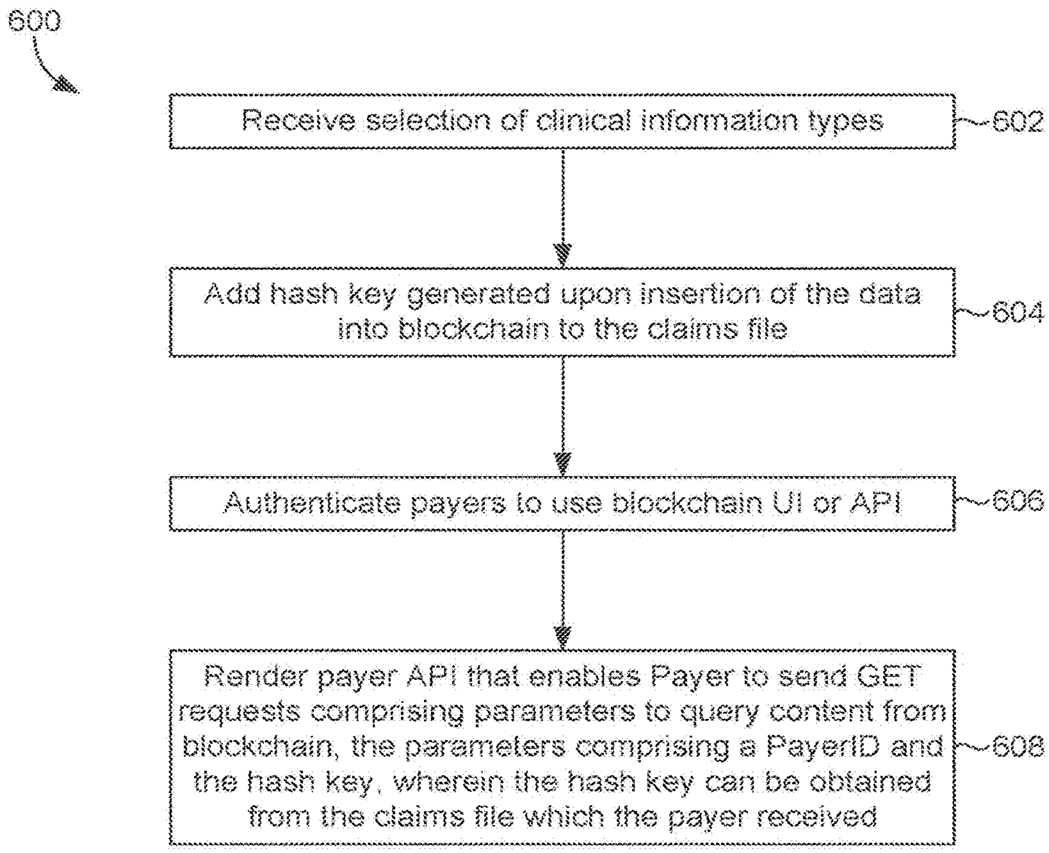
FIG. 6 is a flow diagram of a method for a provider utilizing the interchange system, in accordance with embodiments of the present system/method.

Referring now to FIG. 6, a flow diagram is provided illustrating a method 600 for a provider utilizing the interchange system, in accordance with embodiments of the present system/method. Method 600 may be performed by any computing device (such as computing device described with respect to FIG. 1) with access to an interchange system (such as the one described with respect to FIG. 2) or by one or more components of the interchange system.

Initially, at step at step 602, a DEP tool is utilized to provide the submitter consent and select what clinical data should be displayed or shared with the payer. For example, a submitter may select clinical information types including procedures, demographics, document references, diagnostic reports, and medication orders.

At step 604, a claim module adds a hash key that is generated upon insertion of the data into blockchain to the claims file. For example, each time a claims file is generated involving a submitter and a payer that has subscribed for blockchain, a request is made to the blockchain. The blockchain generates a transaction to store a FHIR URI and a hash corresponding to the submitter and the payer. The hash is also added to the claims file.

At step 606, a gateway authenticates payers attempting to utilize the payer chart review UI or the FHIR API. As can be appreciated, an unsubscribed payer will not have the hash key in the claims file and cannot access the blockchain service. Both the payer and the submitter must be subscribers.

At step 608, a payer API is rendered via the gateway. The payer API enables the payer to send GET requests to query content from the blockchain. The parameters for the HTTP GET request may comprise a PayerID and the hash key. As described, the hash key is obtained by the payer from the claims file the payer received from the submitter.

Many different arrangements of the various components depicted, as well as components not shown, are possible without departing from the spirit and scope of the present system/method. Embodiments of the present system/method have been described with the intent to be illustrative rather than restrictive. Alternative embodiments will become apparent to those skilled in the art that do not depart from its scope. A skilled artisan may develop alternative means of implementing the aforementioned improvements without departing from the scope of the present system/method.

It will be understood that certain features and subcombinations are of utility and may be employed without reference to other features and subcombinations and are contemplated within the scope of the claims. Not all steps listed in the various figures need be carried out in the specific order described. Accordingly, the scope of the system/method is intended to be limited only by the following claims.

What is claimed is:

1. A system for managing access to clinical information associated with a healthcare claim using a blockchain network, the system comprising:

one or more processors; and a non-transitory computer-readable storage medium storing instructions that, when executed by the one or more processors, cause the system to:

receive a healthcare claim file associated with a submitter identifier and a payer identifier, the submitter identifier and the payer identifier being participants of the blockchain network;

generate a pointer record associated with the healthcare claim file, the pointer record being based at least in part on a Fast Healthcare Interoperability Resources (FHIR)-compliant Uniform Resource Identifier (URI) that identifies clinical information that the payer identifier is authorized to access in accordance with consent data stored on the blockchain network;

requesting, by the system, a transaction on the blockchain network to store the pointer record, wherein execution of the transaction by the blockchain network generates a hash key corresponding to the pointer record;

receive, from the blockchain network, the hash key and associate the hash key with the healthcare claim file; and enable access to the clinical information authorized for the payer identifier in response to receiving, from a node associated with the payer identifier, a request including the hash key to obtain the clinical information, wherein access is enabled using the FHIR-compliant URI associated with the pointer record corresponding to the hash key and by validating, by a smart contract executed on the blockchain network, that the payer identifier is authorized to access the clinical information based on the consent data stored on the blockchain network and associated with the submitter identifier and the payer identifier.

2. The system of claim 1, wherein the hash key and the pointer record define a key-value pair stored on the blockchain network, the hash key serving as a unique identifier for the pointer record.

3. The system of claim 1, wherein the pointer record comprises a link or reference to a FHIR application programming interface (API) endpoint configured to retrieve the clinical information from an electronic health record (EHR) system.

4. The system of claim 1, wherein the healthcare claim file is associated with consent data and identifies one or more clinical information types selected for access by the payer identifier, the clinical information types including at least one of procedure data, diagnostic reports, observations, document references, or medication orders.

5. The system of claim 1, wherein the blockchain network is configured to store the pointer record and the hash key while maintaining the clinical information in an origin system not within the blockchain network.

6. The system of claim 1, wherein the hash key comprises a cryptographic hash computed from at least a portion of the payer identifier, submitter identifier, and the pointer record.

7. The system of claim 1, wherein the system is configured to append the hash key to the healthcare claim file transmitted to a payer associated with the payer identifier to enable subsequent blockchain-based retrieval of the clinical information authorized for access with the payer identifier.

8. A computer-implemented method, performed by a computing system, for managing access to clinical information associated with a healthcare claim using a blockchain network, the method comprising:

receiving a healthcare claim file associated with a submitter identifier and a payer identifier, the submitter identifier and the payer identifier being participants of the blockchain network;

generating a pointer record associated with the healthcare claim file, the pointer record being based at least in part on a Fast Healthcare Interoperability Resources (FHIR)-compliant Uniform Resource Identifier (URI) that identifies clinical information that the payer identifier is authorized to access in accordance with consent data stored on the blockchain network;

invoking a transaction on the blockchain network to store the pointer record, wherein execution of the transaction by the blockchain network generates a hash key corresponding to the pointer record;

receiving, from the blockchain network, the hash key and associating the hash key with the healthcare claim file; and enabling access to the clinical information authorized for the payer identifier in response to receiving, from a node associated with the payer identifier, a request including the hash key to obtain the clinical information, wherein access is enabled using the FHIR-compliant URI associated with the pointer record corresponding to the hash key;

wherein enabling access to the clinical information further comprises validating, by a smart contract executed on the blockchain network, that the payer identifier is authorized to access the clinical information based on the consent data stored on the blockchain network and associated with the submitter identifier and the payer identifier.

9. The method of claim 8, further comprising storing the hash key and the pointer record as a key-value pair on the blockchain network, the hash key serving as a unique identifier for the pointer record.

10. The method of claim 8, wherein the pointer record comprises a link or reference to a FHIR application programming interface (API) endpoint configured to retrieve the clinical information from an electronic health record (EHR) system.

11. The method of claim 8, further comprising associating the healthcare claim file with consent data, wherein the consent data identifies one or more clinical information types selected for access by the payer identifier, the clinical information types including at least one of procedure data, diagnostic reports, observations, document references, or medication orders.

12. The method of claim 8, wherein the blockchain network stores the pointer record and the hash key while maintaining the clinical information in an origin system not within the blockchain network.

13. The method of claim 8, wherein the hash key comprises a cryptographic hash computed from at least a portion of the payer identifier, submitter identifier, and the pointer record.

14. The method of claim 8, further comprising appending the hash key to the healthcare claim file transmitted to a payer associated with the payer identifier to enable subsequent blockchain-based retrieval of the clinical information authorized for access with the payer identifier.

15. One or more non-transitory computer storage media having computer-executable instructions embodied thereon that, when executed by a computing system, causes the computing system to perform operations to provide a data interchange, the operations comprising:

receiving a healthcare claim file associated with a submitter identifier and a payer identifier, the submitter identifier and the payer identifier being participants of a blockchain network;

generating a pointer record associated with the healthcare claim file, the pointer record being based at least in part on a Fast Healthcare Interoperability Resources (FHIR)-compliant Uniform Resource Identifier (URI) that identifies clinical information that the payer identifier is authorized to access in accordance with consent data stored on the blockchain network;

invoking a transaction on the blockchain network to store the pointer record, wherein execution of the transaction by the blockchain network generates a hash key corresponding to the pointer record;

receiving, from the blockchain network, the hash key and associating the hash key with the healthcare claim file; and enabling access to the clinical information authorized for the payer identifier in response to receiving, from a node associated with the payer identifier, a request including the hash key to obtain the clinical information, wherein access is enabled using the FHIR-compliant URI associated with the pointer record corresponding to the hash key;

wherein enabling access further comprises validating, by a smart contract executed on the blockchain network, that the payer identifier is authorized to access the clinical information based on consent data associated with the submitter identifier and the payer identifier, wherein the consent data is stored on the blockchain network.

16. The one or more non-transitory computer storage media of claim 15, wherein the pointer record comprises a link or reference to a FHIR application programming interface (API) endpoint configured to retrieve the clinical information from an electronic health record (EHR) system.

17. The one or more non-transitory computer storage media of claim 15, further comprising executable instructions for causing the computing system to associate the healthcare claim file with consent data, wherein the consent data identifies one or more clinical information types selected for access by the payer identifier, the clinical information types including at least one of procedure data, diagnostic reports, observations, document references, or medication orders.

* * * * *